United States Patent
Jin et al.

(10) Patent No.: US 9,490,183 B2
(45) Date of Patent: Nov. 8, 2016

(54) NONDESTRUCTIVE INLINE X-RAY METROLOGY WITH MODEL-BASED LIBRARY METHOD

(71) Applicant: TOKYO ELECTRON LIMITED, Tokyo (JP)

(72) Inventors: Wen Jin, Fremont, CA (US); Junwei Bao, Los Altos, CA (US)

(73) Assignee: Tokyo Electron Limited, Tokyo (JP)

( * ) Notice: Subject to any disclaimer, the term of this patent is extended or adjusted under 35 U.S.C. 154(b) by 4 days.

(21) Appl. No.: 14/714,254

(22) Filed: May 16, 2015

(65) Prior Publication Data

US 2015/0330915 A1 Nov. 19, 2015

Related U.S. Application Data

(60) Provisional application No. 61/994,664, filed on May 16, 2014.

(51) Int. Cl.
| G01N 23/00 | (2006.01) |
| H01L 21/66 | (2006.01) |
| G01N 23/225 | (2006.01) |
| G01N 23/04 | (2006.01) |

(52) U.S. Cl.
CPC ............ *H01L 22/12* (2013.01); *G01N 23/225* (2013.01); *G01N 23/04* (2013.01)

(58) Field of Classification Search
CPC ..... H01L 22/12; G01N 23/225; G01N 23/04
USPC ................................ 378/51, 54, 56
See application file for complete search history.

(56) References Cited

U.S. PATENT DOCUMENTS

| 2008/0255786 A1* | 10/2008 | Jin | ...................... G01N 21/4788 702/81 |
| 2008/0255801 A1* | 10/2008 | Jin | ...................... G03F 7/70625 702/181 |

* cited by examiner

*Primary Examiner* — Michael Maskell
(74) *Attorney, Agent, or Firm* — Oblon, McClelland, Maier & Neustadt, L.L.P.

(57) ABSTRACT

Described is a method and system for measuring parameters of a structure on a substrate, such as a via or a through-silicon via (TSV) using an imaging X-ray metrology system. A previously-trained Support Vector Machine (SVM) model is used to extract structure parameters from the acquired structure X-ray images. Training of the Support Vector Machine (SVM) model is accomplished by using a library of actual or simulated X-ray images, or a combination of the two image types, paired with structure parameter sets.

14 Claims, 4 Drawing Sheets

NONDESTRUCTIVE INLINE X-RAY METROLOGY WITH MODEL-BASED LIBRARY METHOD

CROSS REFERENCE TO RELATED APPLICATIONS

This application is based on and claims the benefit of and priority to co-pending U.S. Provisional Patent Application No. 61/994,664, entitled "NONDESTRUCTIVE INLINE X-RAY METROLOGY WITH MODEL-BASED LIBRARY METHOD" (Ref. No. TTI-243PROV), filed on May 16, 2014, the entire contents of which are herein incorporated by reference.

BACKGROUND OF THE INVENTION

1. Field of the Invention

The present invention relates to a method, computer method, and system for measuring structures formed on semiconductor, or other types of substrates, using X-ray images as input.

2. Description of Related Art

Production of semiconductor devices, displays, photovoltaics, etc., proceeds in a sequence of steps, each step having parameters optimized for maximum device yield. Metrology steps are used during (in-situ) and between various processing steps, to ascertain that device processing is proceeding normally and that target device parameters have been obtained, such as device physical dimensions, electrical and other properties, etc. If not obtained, metrology allows for early identification of failing processes allowing early redirection of mis-processed devices to a rework process flow, or discarding thereof.

Modern semiconductor packages pack a large number of devices into a single packaging, and one way to increase the packaging density is to use three-dimensional (3D) stacking of semiconductor die. To establish electrical connections between the individual die in such a package, through-silicon vias (TSV) are often used. A TSV is an opening created in the semiconductor die, generally from one side of the die to the other side. The TSV is typically filled with metal conductor, such as copper, to establish an electrical connection between the devices formed on the die, and another set of devices formed atop another die beneath the first die. Stacking many layers of die allows many billions of individual devices to be packaged into a package that requires a relatively small area on the circuit board atop which it is mounted.

To ensure that target electrical performance of TSVs is obtained during processing, metrology steps are used to monitor the TSV-formation processes. Because the process of formation of TSVs involves etching of very high aspect-ratio vias, monitoring the dimensions of TSVs formed on the die is of particular importance. Existing methods use electron microscopy to accomplish this task, some of which methods are destructive in nature (i.e. they require sample die to be cleaved to inspect the TSV dimensions), and some of which are nondestructive. But, the biggest issue is a process throughput reduction associated with redirecting samples for inspection, to a standalone electron microscope.

Therefore, the need exists for TSV metrology and inspection with high throughput, preferably integrated with the etching tool, and which is nondestructive. For TSVs, which are of relatively large size compared to contemporary semiconductor gate devices themselves, X-ray metrology is a candidate metrology that may provide the above benefits.

One X-ray based metrology method is X-ray tomography, widely used in biological and medical sciences, which allows a full reconstruction of a three-dimensional structure formed on a semiconductor substrate. However, X-ray tomography requires that very many line-of-sight X-ray images be taken such that a full representation of the structure can be constructed, which reduces throughput, thus rendering the method unsuitable for in-situ process monitoring.

Today, advances in X-ray sources and planar pixel X-ray detectors now allow sufficient resolution for micron-scale TSVs to be inspected by simple imaging. What is needed is a method to quickly extract the dimensions of TSVs from simple X-ray images, concurrent with the etch process, such that the acquired metrology data can be used to alter etch (and other) process parameters, with the goal of maintaining target device properties during device processing.

SUMMARY OF THE INVENTION

An aspect of the invention includes a method for measuring a structure on a substrate, comprising: forming a Support Vector Machine (SVM) machine learning model that correlates a transmitted X-ray signal through the structure and at least one parameter of the structure; irradiating the structure with X-ray radiation from an X-ray source; acquiring a transmitted X-ray radiation signal from an X-ray detector; and calculating the at least one parameter of the measured structure by applying the Support Vector Machine (SVM) machine learning model to the acquired transmitted X-ray radiation signal. The transmitted X-ray radiation signal may comprise an X-ray image, and the at least one calculated structure parameter may comprise a critical dimension (CD) of a via, a thickness (depth) of a via, or a sidewall angle of a via.

A further aspect of the invention involves the step of forming the Support Vector Machine (SVM) machine learning model comprising: providing a training set of transmitted X-ray signals; providing a training set of structure parameters corresponding to the training set of transmitted X-ray signals; forming a library of correlated transmitted X-ray signals and structure parameters, and training the Support Vector Machine (SVM) machine learning model using the library data as a training data set. Transmitted X-ray signals may comprise simulated X-ray signals, measured X-ray signals, or a combination thereof, and the Support Vector Machine (SVM) machine learning model training may utilize cross validation.

Furthermore, various preprocessing steps may be performed on the transmitted X-ray signals used for Support Vector Machine (SVM) training and during actual device parameter measurements. Preprocessing steps may include single structure extraction steps (from larger multi-structure images), image data extraction (such as extracting individual image pixel scan-lines), and reduction of the number of dimensions of the extracted data.

Yet a further aspect of the invention includes a non-transitory machine-readable storage medium having instructions stored thereon which cause a computer to perform the methods associated with the aforementioned aspects of the invention.

A further aspect of the invention includes a system for measuring a structure on a substrate, comprising: an X-ray source; an X-ray detector; a stage for receiving a substrate; and a controller for controlling the X-ray source, X-ray detector, and stage for receiving the substrate, wherein the controller is configured to calculate at least one parameter of the measured structure by applying a previously-formed Support Vector Machine (SVM) machine learning model to an acquired transmitted X-ray radiation signal obtained by irradiating the substrate with X-ray radiation from the X-ray source, and acquiring the transmitted X-ray radiation signal using the X-ray detector, and wherein the Support Vector Machine (SVM) machine learning model correlates the transmitted X-ray signal through the structure and the at least one parameter of the structure.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF EXEMPLARY EMBODIMENTS

In the following description, in order to facilitate a thorough understanding of the invention and for purposes of explanation and not limitation, specific details are set forth of a method and system for measuring structure properties using a TSV X-ray metrology system. However, it should be understood that the invention may be practiced in other embodiments that depart from these specific details.

In the description to follow, the term substrate, which represents the workpiece being processed, may be used interchangeably with terms such as semiconductor wafer, LCD panel, light-emitting diode (LED), photovoltaic (PV) device panel, etc., the processing of all of which falls within the scope of the claimed invention.

Reference throughout this specification to "one embodiment" or "an embodiment" means that a particular feature, structure, material, or characteristic described in connection with the embodiment is included in at least one embodiment of the invention, but do not denote that they are present in every embodiment. Thus, the appearances of the phrases "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Various operations will be described as multiple discrete operations in turn, in a manner that is most helpful in understanding the invention. However, the order of description should not be construed as to imply that these operations are necessarily order dependent. In particular, these operations need not be performed in the order of presentation. Operations described may be performed in a different order than the described embodiment. Various additional operations may be performed and/or described operations may be omitted in additional embodiments.

Figure 1:
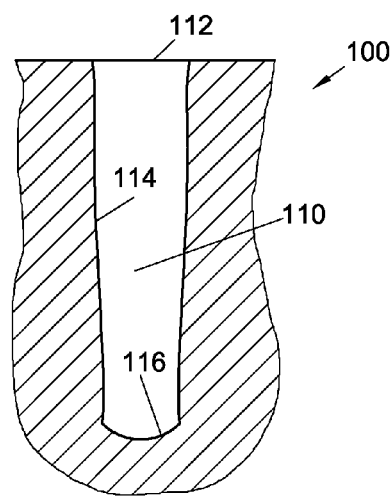
FIG. 1 shows a typical through-silicon via (TSV) formed in a substrate.

FIG. 1 shows a typical high-aspect ratio through-silicon via (TSV) 110 formed in a substrate 100, which may be made of a semiconductor material, such as silicon, or any other material suitable for use as a substrate for forming microdevices. TSV 110 comprises a sidewall 114 and has an opening 112 facing above the substrate 100, typically a direction from which an etching plasma is applied to the substrate 100 to form TSVs 110. The TSV 110 has a bottom 116, depicted here at an intermediate stage of processing. Typical final TSV 110 configurations involve extending the TSV 110 until it forms an opening on the opposite side of the substrate. Dimensions of TSVs 110 vary depending on the application and packing density of electrical connections extending between the die that the electrical connections are intended to connect. For example, the thickness (or depth) of a TSV may vary from 20 µm to well above 500 µm, depending on the thickness of the substrate 100. Diameters (or critical dimensions, or CDs, as they are also called) can vary from 5 µm to 50 µm. Generally, TSVs 110 of large diameter are used in cases where the substrate thickness is large, such that the conductor formed by filling the TSV 110 can have a low resistance (as related to the cross section and length of the conductor.)

It should be noted here that the foregoing discussion and all discussion hereinafter applies equally to ordinary vias, such as those used as contacts for actual gates on semiconductor devices, provided the X-ray metrology system has a sufficient resolution to resolve such, typically much smaller structures. Furthermore, the concepts can be extended to measurement of yet other structures, such as trenches, interconnect structures, contacts, pads, gates, etc.

Figure 2:
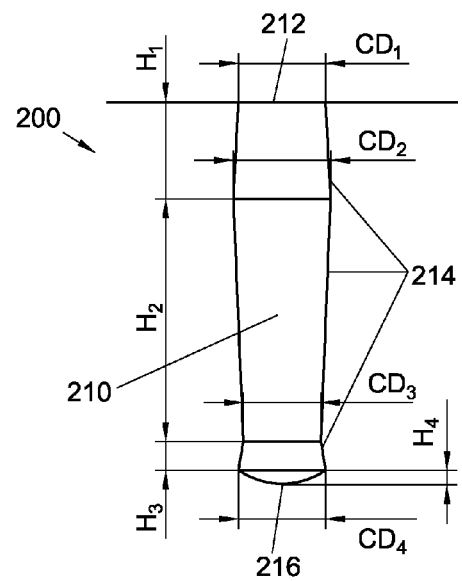
FIG. 2 shows a model of a TSV in accordance with an embodiment of the invention.

In metrology applications, it is frequently suitable to model a structure, such as a via or a TSV 110 using a finite set of dimensional parameters. FIG. 2 shows an exemplary model in which TSV 210 is modeled, or described, using eight independent parameters: four critical dimensions (i.e. diameters) $CD_1$, $CD_2$, $CD_3$, and $CD_4$, and four thicknesses (i.e. depths) $H_1$, $H_2$, $H_3$, and $H_4$. An X-ray metrology system would thus be expected to be capable of measuring these eight parameters. Some applications where structure dimensions are of more importance may require more dimensions to be measured and controlled, while some applications may require less (in the simplest case, for example, a TSV 210 may be described with just one CD and one thickness H.) Additional parameters, such as the sidewall angle (SWA) may also be measured by the metrology system, using the method and system discussed hereinafter. The TSV 210 of FIG. 2 has an opening 212, sidewall 214 (divided into regions), and a bottom 216. Usually, at the conclusion of etching, the TSV 210 may extend through the entire thickness of the substrate (not shown), and thus the structure depicted in FIG. 2 represents a structure at an intermediate stage of etch processing, as may be measured, for example, by an in-situ metrology system.

Figure 3:
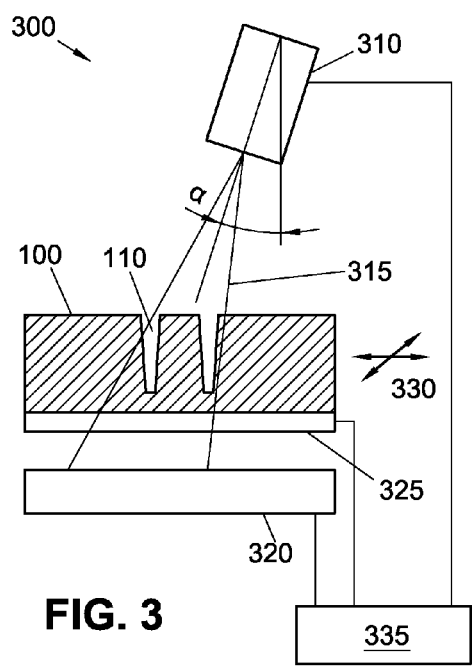
FIG. 3 shows an TSV X-ray metrology system in accordance with an embodiment of the invention.

FIG. 3 shows a schematic of a TSV X-ray metrology system 300, comprising an X-ray source 310, a stage 325 for receiving the substrate 100 with TSVs 110 being formed thereupon, and an X-ray detector 320. The X-ray source 310 can be any suitable X-ray source, such as for example a Hamamatsu Photonics Nano-Focus metal pillar target X-ray source with a 1 μm Gaussian point spread function (PSF) and a spatial resolution of about 0.25 μm. The X-ray detector 320 can be a suitable X-ray camera, such as a Hamamatsu Photonics CMOS image-intensified X-ray camera, with a 1920×1440 pixel array (2.8 mega-pixel, actual device size being 6.97 mm×5.23 mm, with 3.63 μm square pixels). The X-ray source 310 forms a conical X-ray beam 315, and the X-ray source may be mounted at an angle α off normal incidence, such that images of the TSVs 110 contain sufficient information about sidewalls 114 and bottoms 116 of TSVs 110. The angle of incidence a may be variable, and a typical angle used is between 0 and about 15°, but can vary from 0 to 30°. The spacings from the substrate 100 (and stage 325) to the X-ray detector 320 and from the substrate 100 to the X-ray source 310 can be adjusted to achieve a magnification in the range from 20 to 300, for example, enabling high resolution TSV imaging with the selected X-ray detector 320. The stage 325 can be moved in two directions 330, by means of a suitable motorized stage (not shown) such that structures being measured can be centered within the X-ray beam 315 and on X-ray detector 320. A controller 335 is operably connected to all of the components of TSV X-ray metrology system 300, and has multiple functions including at least: controlling X-ray source 310, controlling X-ray detector 320 and acquiring images therefrom, controlling spacings and/or magnification and stage 325 position, and processing acquired X-ray images to extract TSV 110 parameters, for example the eight parameters shown in FIG. 2, as will be described hereinafter.

Figure 4:
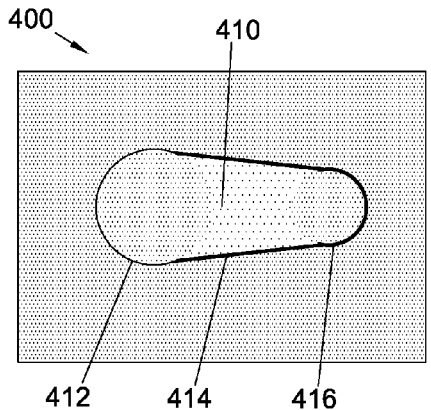
FIG. 4 shows an exemplary image of a TSV obtained using a TSV X-ray metrology system in accordance with an embodiment of the invention.

FIG. 4 shows what a typical X-ray image 400 of a TSV 410 (such as TSV 110 of FIG. 1) may look like. This X-ray image 400 may be extracted (cut out) of a larger X-ray image acquired by X-ray detector 320, and may have a resolution of, for example, 300×200 pixels, depending on the size of TSVs 410, the magnification setting, resolution of X-ray detector 320, etc. The image may be, for example, a 16 bit gray scale image, thus with 65536 levels of gray, depending on the type of X-ray detector 320 and the A/D converters used to digitize the detector signal.

Features such as the TSV opening 412, sidewall 414, and bottom 416, of TSV 410 are readily discernible from the X-ray image 400. An embodiment of the invention includes a method for extracting parameters of TSV 410, such as parameters $CD_1$, $CD_2$, $CD_3$, $CD_4$, $H_1$, $H_2$, $H_3$, and $H_4$, of FIG. 2, from X-ray images such as X-ray image 400.

Figure 5:
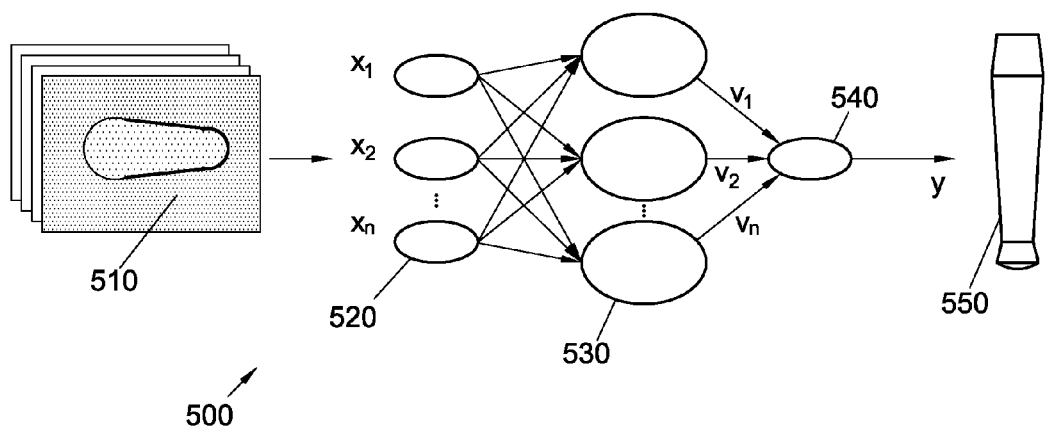
FIG. 5 shows a schematic of a Support Vector Machine (SVM) machine learning model used for TSV X-ray metrology, in accordance with an embodiment of the invention.

In an embodiment, a Support Vector Machine (SVM) machine learning model is used to extract parameters from X-ray images 400. FIG. 5 shows a schematic of the Support Vector Machine (SVM) machine learning model 500, which uses a set of images 510 (comprising X-ray images 400, for example) as an input $x_1, x_2, \ldots x_n$ to a previously-trained Support Vector Machine (SVM) machine learning model comprising nodes 520 and 540, and utilizing kernel functions 530 to produce an output vector y of parameters of TSVs 410 captured in images 510, thus constructing a model 550 of the TSV 410 (similar to model 200 of FIG. 2.) Node 540 of the SVM combines the contributions from previous SVM node layers to form the output vector y. Output vector y may contain parameters $CD_1$, $CD_2$, $CD_3$, $CD_4$, $H_1$, $H_2$, $H_3$, and $H_4$, of FIG. 2, but may also contain less parameters, or more parameters, depending on how the SVM was trained (which in turn, depends on the demands of the application.)

Images 510 may be pre-processed prior to being used as input $x_1, x_2, \ldots x_n$ to the Support Vector Machine (SVM) machine learning model 500. For example, the images may contain multiple structures, and an identification algorithm may be used to extract images of a single structure, for metrology. The input data to the Support Vector Machine (SVM) machine learning model 500 may be a full X-ray image 400 from image set 510, but it may also be data related to a feature extracted from the individual X-ray images 400. For example, a feature may be an array of pixel intensities along a line of pixels within the X-ray image 400, which may be used as input in lieu of the entire X-ray image 400 provided sufficient information is retained in the pixel intensities of the extracted array of pixels. Lastly, to facilitate training and increase the efficiency and accuracy of the Support Vector Machine (SVM) machine learning model 500, the inputs $x_2, \ldots x_n$ may be dimensionally reduced. For example, a method such as Principal Components Analysis (PCA), or similar, can be used to reduce the number of inputs $x_1, x_2, \ldots x_n$ while retaining all of the relevant information extracted from the image. All of these steps are optional, but the inventors have determined that the investment in computing time on preprocessing generally pays off well in terms of increasing the computational efficiency of the Support Vector Machine (SVM) machine learning model 500. Inventors have been able to reduce the computational time of parameter vector y from X-ray images 400 to approximately 1 second, using an ordinary personal computer as controller 335, which renders this method uniquely suitable for in-situ and in-line monitoring of etch processes, as would, for example, be the case where the TSV X-ray metrology system 300 were included as a module within an etch tool.

The kernel functions 530 of the Support Vector Machine (SVM) machine learning model 500 may be Radial Basis Function (RBF) kernel functions K of the form $$K(x_i, x_j) = \exp\frac{-\|x_i - x_j\|}{2\sigma^2},$$

wherein the transfer function of the Support Vector Machine (SVM) machine learning model 500 can be expressed as $$y = \sum_{i=1}^{s} v_i K(x_i, Z_{realdata}) + b,$$

where $v_i$ are weights $v_1, v_2, \ldots v_n$, and b is a constant.

Prior to using the Support Vector Machine (SVM) machine learning model 500, the machine learning model needs to be trained to establish the values of all parameters of the Support Vector Machine (SVM) machine learning model 500. Training of Support Vector Machine (SVM) machine learning model 500 is accomplished by providing pairs of an X-ray image associated with a set of structure parameters. If the number of pairs provided for training of Support Vector Machine (SVM) machine learning model 500 is sufficiently large and the structure parameters vary over ranges of values expected of these parameters in real device processing, then the Support Vector Machine (SVM) machine learning model 500 can be used for TSV X-ray metrology, as outlined in FIG. 5.

Input data for training of the Support Vector Machine (SVM) machine learning model 500 can come from a variety of sources. In an embodiment, the X-ray image and structure parameter data pairs can be obtained from real manufactured devices that have been imaged using TSV X-ray metrology system 300, and whose structure parameters, such as parameters $CD_1$, $CD_2$, $CD_3$, $CD_4$, $H_1$, $H_2$, $H_3$, and $H_4$, of FIG. 2, have been measured using another method, such as transmission electron microscopy (X-SEM, T-SEM). The disadvantage of this method is that a large number of samples need to be prepared and measured in order to establish the training data set.

An alternative is to provide simulated training data. If the parameters of a structure are known, as they would be in the case of a simulation where parameters are varied over given ranges, then the actual X-ray image, such as X-ray image 400 may be obtained by simulating the transmission, reflection, and scattering of X-rays from a modeled structure. Such a simulation can be done, for example, by creating a full three-dimensional model of the structure, in this case a TSV 210, and subdividing the computational domain into volume pixels, or "voxels". Then, an incident X-ray beam is tracked by computer simulation as it traverses the simulated three-dimensional structure discretized into voxels, with effects such as transmission, reflection, and scattering taken into account. The transmitted portion (across substrate model 200) of the simulated X-ray beam is then used to calculate a simulated X-ray image 400, which along with parameters of the simulated structure forms a pair suitable for training of the Support Vector Machine (SVM) machine learning model 500. With a sufficient number of simulated pairs, with varying parameters, a library can be formed, and the library can be used for SVM training. Typical library sizes range from 1000 to up to about 10000 image and structure parameter set pairs, but the inventors have shown that useful Support Vector Machine (SVM) machine learning models 500 can be obtained with up to about 5000 pairs, and in some cases even as low as 3000 pairs.

Training of the Support Vector Machine (SVM) machine learning models 500 can be done with cross validation, as is customarily done with SVMs to evaluate the robustness of the generated model. Implementations of Support Vector Machine (SVM) algorithms are provided by many vendors of scientific software. An example of such software is Matlab and its Machine Learning modules, which are available from MathWorks, Inc. of 3 Apple Hill Drive, Natick, Mass., USA.

Figure 6:
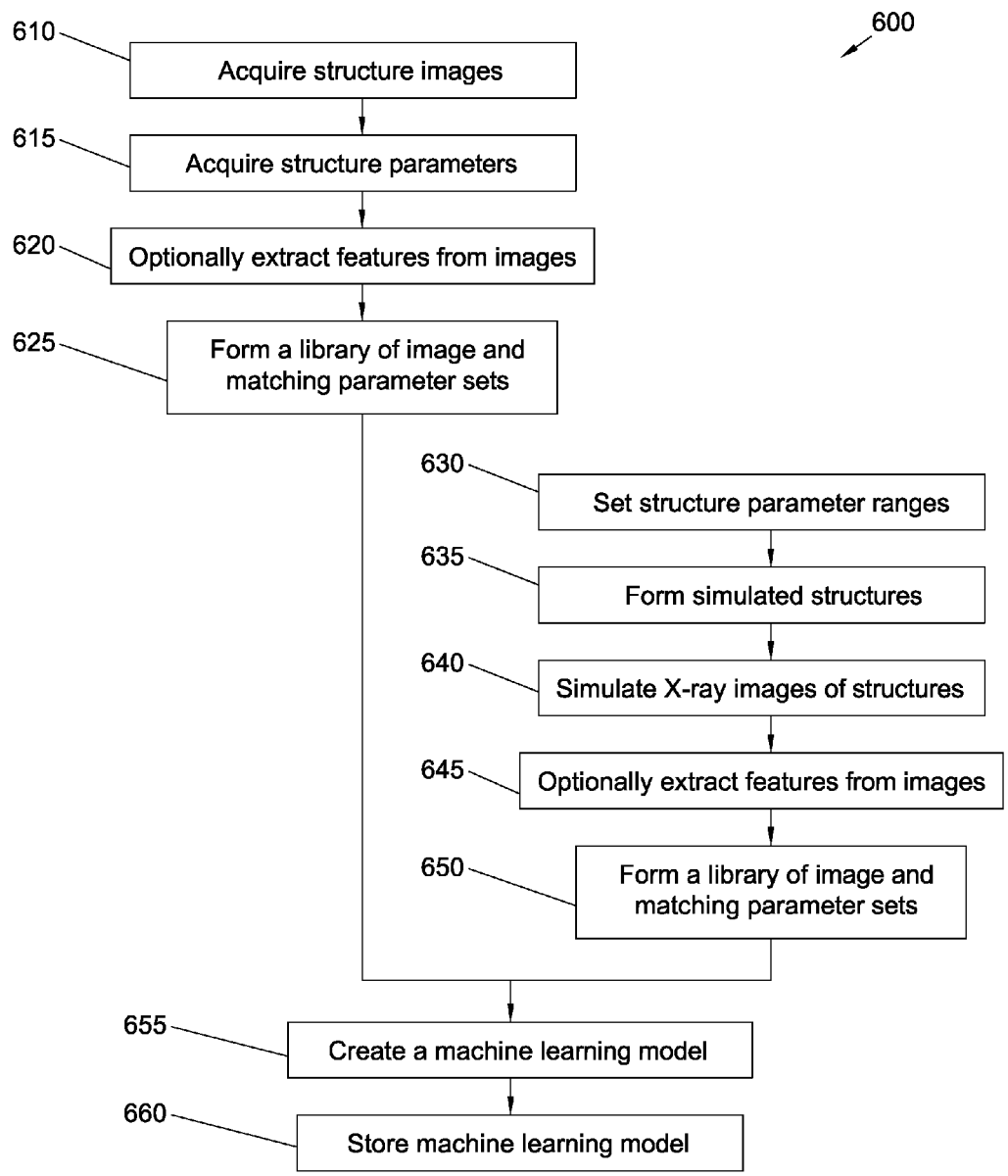
FIG. 6 shows a flowchart of a process of training a Support Vector Machine (SVM) to form a machine learning model to be used for TSV X-ray metrology, in accordance with an embodiment of the invention.

Now that the measurement and training processes have been described, FIG. 6 shows a flowchart of the process 600 of training the Support Vector Machine (SVM) machine learning models 500. As mentioned before, the training input data may be obtained experimentally or via simulation, and thus the flowchart has two input flows depending on the type of data. In practice, mixed experimental and simulated data may be used, as well.

In the case of using actual experimentally acquired images, the process begins at step 610 in which X-ray images 400 are acquired of TSVs 110 formed on substrate(s) 100, using TSV X-ray metrology system 300, wherein the structure parameters cover relevant ranges of parameters, for example parameters $CD_1$, $CD_2$, $CD_3$, $CD_4$, $H_1$, $H_2$, $H_3$, and $H_4$, of FIG. 2. For example, $CD_1$ may be varied from a minimum value to a maximum value, in a number of steps, the number of steps being determined such that the expected parameter space is well-covered for a given number of data sets used to train the model. For example, $CD_1$ may be varied in about 10 steps, and similar numbers of steps may be used for other parameters.

In step 615, the actual structures, i.e. TSVs 110 are measured using some destructive or nondestructive measurement method, to determine the actual values of the parameter set associated with TSV 110. As mentioned before, many different metrology methods may be used to accomplish the measurement, such as transmission electron microscopy (T-SEM, X-SEM), optical digital profilometry (ODP), simple optical microscopy (for larger TSVs 110), etc. A measured parameter set is now associated with each acquired TSV X-ray image 400, forming a pair.

In step 620, the images acquired in step 610 may be preprocessed and features may be optionally extracted from the images, to reduce the input data size and increase model efficiency. In addition, Principal Components Analysis (PCA) or similar methods may be applied to the extracted data, to further reduce the input data size.

In step 625, a library is formed of all pairs of extracted and optionally preprocessed data from TSV X-ray images 400, and measured parameter sets obtained in step 615. The library is now ready for training of a Support Vector Machine (SVM) machine learning model 500.

In case of using simulation data to form the library, the method begins at step 630 in which a set of ranges of parameters $CD_1$, $CD_2$, $CD_3$, $CD_4$, $H_1$, $H_2$, $H_3$, and $H_4$ of TSVs 210 of FIG. 2 is defined, for example.

In step 635, models of TSVs 210 are formed, while varying parameters within ranges set in step 630.

In step 640, X-ray images 400 of TSVs 210 are formed by using X-ray transmission simulations, as explained before.

In step 645, preprocessing may be done and features may be optionally extracted from simulated TSV X-ray images 400, in the same manner as described with respect to step 620.

In step 650, a library is formed of all pairs of extracted and optionally preprocessed data from TSV X-ray images 400, and parameter sets used for simulation defined in step 630. The library is now ready for training of a Support Vector Machine (SVM) machine learning model 500.

Independent of the type of library being used, i.e. experimental or simulated, the training method now continues in step 655 where the library data is used to train the Support Vector Machine (SVM) machine learning model 500. In this step, all relevant parameters of the SVM model are determined, to enable conversion of image data into a parameter set when the SVM model is applied to image data, as used for actual metrology.

Lastly, the training method concludes at step 660, wherein the parameters of Support Vector Machine (SVM) machine learning model 500 are stored in volatile or nonvolatile storage media on controller 335 of TSV X-ray metrology system 300, for use in later measurements.

Figure 7:
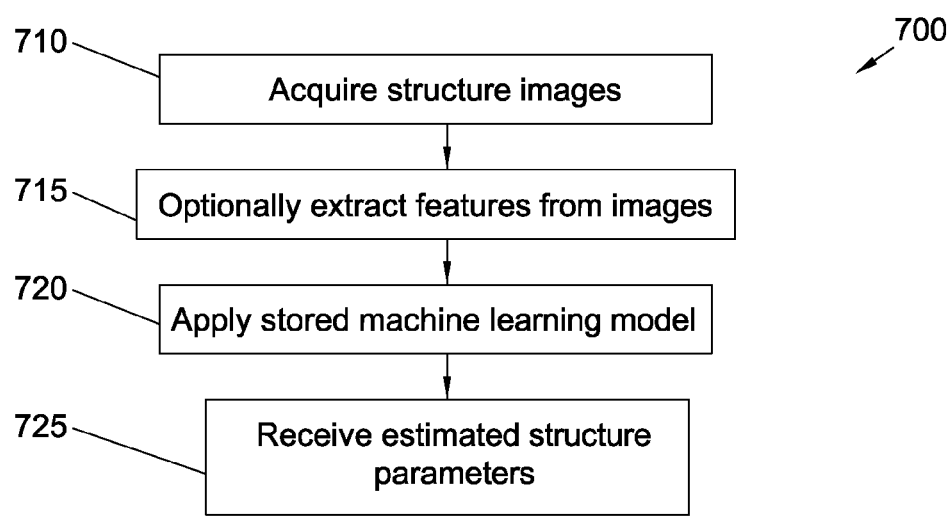
FIG. 7 shows a flowchart of a process of measuring TSVs using TSV X-ray metrology that utilizes a Support Vector Machine (SVM) machine learning model in accordance with an embodiment of the invention.

FIG. 7 shows the simple method 700 by which the stored Support Vector Machine (SVM) machine learning model 500, with its trained and stored parameters determined in steps 655 and 660, above, is used for measuring TSVs of unknown size.

The method commences at step 710 in which X-ray images 400 are acquired of TSVs 110 formed on substrate(s) 100, using TSV X-ray metrology system 300.

In step 715, the X-ray images 400 may be preprocessed and features may be optionally extracted from them in the same manner as described with respect to step 620. It is important to note that if the model has been trained with images preprocessed and features extracted in a certain way, then the images acquired in this step have to be preprocessed and features extracted in the exact same way. Otherwise, the method will not produce satisfactory results.

In step 720, the Support Vector Machine (SVM) machine learning model 500 is applied to data prepared in step 715, the output of the process being parameter sets y which may comprise, for example, parameters $CD_1$, $CD_2$, $CD_3$, $CD_4$, $H_1$, $H_2$, $H_3$, and $H_4$ of FIG. 2. The calculated parameters represent the output of the TSV X-ray metrology method, and they may be stored, transmitted, received, displayed, used for process control in a feedback and feedforward manner, within die, within wafer, from wafer lot to wafer lot, etc.

Step 725 that concludes the TSV X-ray metrology method.

Now will be presented some results of the use of the method and system as described in the foregoing discussion.

In the first evaluation, TSVs with a nominal total thickness (i.e. total depth $H_1+H_2+H_3+H_4$) of 50 μm were formed, X-ray imaged, and measured. The results of the evaluation are shown in TABLE 1.

TABLE 1

TSV X-ray metrology evaluation for 50 μm TSVs

| Parameter | X-SEM [μm] | X-ray metrology [μm] |
|---|---|---|
| $CD_1$ | 5.25 | 5.54 |
| $CD_2$ | 5.02 | 5.27 |
| $CD_3$ | 3.93 | 4.48 |
| $CD_4$ | 2.74 | 3.29 |
| $H_1 + H_2 + H_3 + H_4$ | 52.07 | 51.15 |

The results immediately show the potential value of the TSV X-ray metrology method. For example, the thickness (total depth) measurement is accurate to within 1 μm of the value determined using electron microscopy (X-SEM), but the measurement can be obtained in-line in about 1 second instead of the long off-line process typically required for X-SEM measurement. For diameters, i.e. CDs, the data is somewhat less accurate, i.e. when comparing the mean values displayed in the table. The correlation coefficient $R^2$ between X-SEM and X-ray metrology data for the four CDs evaluates to 0.9946, and the 3σ values for the four CDs (using 10 measurements for each) are 0.04405 μm, 0.03062 μm, 0.15092 μm, 0.07473 μm, respectively, and 0.52827 μm for the total thickness.

In the second evaluation, TSVs with a nominal total thickness (i.e. total depth $H_1+H_2+H_3+H_4$) of 75 μm were formed, X-ray imaged, and measured. The results of the evaluation are shown in TABLE 2.

TABLE 2

TSV X-ray metrology evaluation for 75 μm TSVs

| Parameter | X-SEM [μm] | X-ray metrology [μm] |
|---|---|---|
| $CD_1$ | 5.51 | 5.86 |
| $CD_2$ | 4.85 | 5.35 |
| $CD_3$ | 3.72 | 4.35 |
| $CD_4$ | 3.2 | 3.4 |
| $H_1 + H_2 + H_3 + H_4$ | 77.1 | 76.1 |

The correlation coefficient $R^2$ between X-SEM and X-ray metrology data for the four CDs evaluates to 0.9715, and the 3σ values for the four CDs (using 10 measurements) are 0.01757 μm, 0.01172 μm, 0.01649 μm, 0.081516 μm, respectively, and 0.12818 μm for the total thickness.

In the last evaluation, TSVs with a nominal total thickness (i.e. total depth $H_1+H_2+H_3+H_4$) of 90 μm were formed, X-ray imaged, and measured. The results of the evaluation are shown in TABLE 3.

TABLE 3

TSV X-ray metrology evaluation for 90 μm TSVs

| Parameter | X-SEM [μm] | X-ray metrology [μm] |
|---|---|---|
| $CD_1$ | 4.16 | 4.35 |
| $CD_2$ | 4.1 | 4.45 |
| $CD_3$ | 3.14 | 3.43 |
| $CD_4$ | 2.59 | 2.75 |
| $H_1 + H_2 + H_3 + H_4$ | 86.65 | 84.7 |

The correlation coefficient $R^2$ between X-SEM and X-ray metrology data for the four CDs evaluates to 0.9946.

Clearly, the measurement results are of better accuracy when the total thickness (total depth) of the TSV is larger, but the results show a lot of potential for use as an in-situ or in-line metrology for 3D interconnect, i.e. through-silicon vias (TSVs).

Persons skilled in the relevant art can appreciate that many modifications and variations are possible in light of the above teaching. Persons skilled in the art will recognize various equivalent combinations and substitutions for various components shown in the figures. It is therefore intended that the scope of the invention be limited not by this detailed description, but rather by the claims appended hereto.

What is claimed is:

1. A method for measuring a structure on a substrate, comprising:
    forming a Support Vector Machine (SVM) machine learning model that correlates a transmitted X-ray signal through the structure and at least one parameter of the structure;
    irradiating the structure with X-ray radiation from an X-ray source;
    acquiring a transmitted X-ray radiation signal from an X-ray detector; and
    calculating the at least one parameter of the measured structure by applying the Support Vector Machine (SVM) machine learning model to the acquired transmitted X-ray radiation signal.

2. The method of claim 1, wherein the transmitted X-ray radiation signal comprises an X-ray image.

3. The method of claim 1, wherein the structure is a via.

4. The method of claim 1, wherein the structure is a through-silicon via (TSV).

5. The method of claim 1, wherein the calculated at least one parameter of the measured structure comprises a critical dimension (CD) of a via, a thickness of a via, or a sidewall angle of a via.

6. The method of claim 1, wherein the step of the forming the Support Vector Machine (SVM) machine learning model comprises:
    providing a training set of transmitted X-ray signals;
    providing a training set of structure parameters corresponding to the training set of transmitted X-ray signals;
    forming a library of correlated transmitted X-ray signals and structure parameters, and
    training the Support Vector Machine (SVM) machine learning model using the library data as a training data set.

7. The method of claim 6, wherein the Support Vector Machine (SVM) machine training utilizes cross validation.

8. The method of claim 6, wherein the training set of transmitted X-ray signals comprises simulated X-ray signals.

9. The method of claim 6, wherein the training set of transmitted X-ray signals comprises measured X-ray signals.

10. The method of claim 9, wherein the training set of structure parameters is measured using transmission electron microscopy.

11. The method of claim 6, wherein the training set of transmitted X-ray signals comprises from about 1000 to about 10000 transmitted X-ray signals.

12. The method of claim 6, wherein the training set of transmitted X-ray signals comprises from about 1000 to about 5000 transmitted X-ray signals.

13. A system for measuring a structure on a substrate, comprising:
   an X-ray source;
   an X-ray detector;
   a stage for receiving a substrate; and
   a controller for controlling the X-ray source, X-ray detector, and stage for receiving the substrate,
   wherein the controller is configured to calculate at least one parameter of the measured structure by applying a previously-formed Support Vector Machine (SVM) machine learning model to an acquired transmitted X-ray radiation signal obtained by irradiating the substrate with X-ray radiation from the X-ray source, and acquiring the transmitted X-ray radiation signal using the X-ray detector, and
   wherein the Support Vector Machine (SVM) machine learning model correlates the transmitted X-ray signal through the structure and the at least one parameter of the structure.

14. A non-transitory machine-readable storage medium having instructions stored thereon which cause a computer to perform a method for measuring a structure on a substrate, comprising:
   forming a Support Vector Machine (SVM) machine learning model that correlates a transmitted X-ray signal through the structure and at least one parameter of the structure;
   irradiating the structure with X-ray radiation from an X-ray source;
   acquiring a transmitted X-ray radiation signal from an X-ray detector; and
   calculating the at least one parameter of the measured structure by applying the Support Vector Machine (SVM) machine learning model to the acquired transmitted X-ray radiation signal.

* * * * *